United States Patent
Prince et al.

(10) Patent No.: US 11,911,140 B2
(45) Date of Patent: Feb. 27, 2024

(54) MEDICAL DEVICE MAGNETIZER

(71) Applicant: Bard Access Systems, Inc., Salt Lake City, UT (US)

(72) Inventors: Matthew J. Prince, Herriman, UT (US); Tab Robbins, Layton, UT (US); Amir Orome, Sandy, UT (US); Bart Peterson, Farmington, UT (US); Bradley M. Wilkinson, North Haledon, NJ (US)

(73) Assignee: Bard Access Systems, Inc., Salt Lake City, UT (US)

( * ) Notice: Subject to any disclaimer, the term of this patent is extended or adjusted under 35 U.S.C. 154(b) by 48 days.

(21) Appl. No.: 17/521,680

(22) Filed: Nov. 8, 2021

(65) Prior Publication Data

US 2022/0142501 A1   May 12, 2022

Related U.S. Application Data

(60) Provisional application No. 63/111,498, filed on Nov. 9, 2020.

(51) Int. Cl.
*H01F 13/00* (2006.01)
*A61B 5/06* (2006.01)
(Continued)

(52) U.S. Cl.
CPC .............. *A61B 5/062* (2013.01); *A61B 34/20* (2016.02); *H01F 7/0221* (2013.01);
(Continued)

(58) Field of Classification Search
CPC ........ H01F 13/00; H01F 13/003; A61B 5/062
(Continued)

(56) References Cited

U.S. PATENT DOCUMENTS

| 3,409,853 | A |   | 11/1968 | Guerth |
| 3,467,926 | A | * | 9/1969 | Smith ................ H01F 13/00 335/284 |

(Continued)

FOREIGN PATENT DOCUMENTS

| CN | 105025787 A | 11/2015 |
| CN | 105232047 A | 1/2016 |

(Continued)

OTHER PUBLICATIONS

PCT/US2021/058478 filed Nov. 8, 2021 International Search Report and Written Opinion dated Mar. 1, 2022.
(Continued)

*Primary Examiner* — Ramon M Barrera
(74) *Attorney, Agent, or Firm* — Rutan & Tucker LLP (57) ABSTRACT

Disclosed herein is a system, apparatus and method directed to a magnetizer comprising at least one magnet; and a housing, the housing comprising: a top face; a bottom face positioned on an opposite side of the housing from the top face; a plurality of faces adjoining the top face and the bottom face; an interior comprising an interior surface formed at least in part by the top face, the bottom face and the plurality of faces; wherein the top face includes a first opening configured to receive a medical device; and wherein the at least one magnet is positioned within the interior of the housing. A face of the plurality of faces may include a second opening to expose at least a portion of the interior surface through the second opening. The second opening may be larger than the first opening.

28 Claims, 2 Drawing Sheets

(51) Int. Cl.
*A61B 34/20* (2016.01)
*H01F 7/02* (2006.01)
*A61B 90/70* (2016.01)

(52) U.S. Cl.
CPC .......... *H01F 7/0294* (2013.01); *H01F 13/00* (2013.01); *A61B 2034/2063* (2016.02); *A61B 90/70* (2016.02)

(58) Field of Classification Search
USPC ....................................................... 335/284
See application file for complete search history.

(56) References Cited

U.S. PATENT DOCUMENTS

| | | |
|---|---|---|
| 3,847,157 A | 11/1974 | Caillouette et al. |
| 4,063,561 A | 12/1977 | McKenna |
| 4,161,943 A | 7/1979 | Nogier |
| 4,237,518 A | 12/1980 | Krulwich |
| 4,458,705 A | 7/1984 | Cawood |
| 4,529,954 A | 7/1985 | Steingroever et al. |
| 5,055,813 A | 10/1991 | Johnson |
| 5,659,279 A | 8/1997 | Janssen et al. |
| 5,803,089 A | 9/1998 | Ferre et al. |
| 5,845,646 A | 12/1998 | Lemelson |
| 6,154,352 A | 11/2000 | Atallah |
| 6,249,199 B1 * | 6/2001 | Liu .................. H01F 13/00 335/284 |
| 6,310,532 B1 | 10/2001 | Santa Cruz et al. |
| 6,432,036 B1 | 8/2002 | Kim |
| 7,023,309 B2 | 4/2006 | Laskaris et al. |
| 7,090,639 B2 | 8/2006 | Govari |
| 7,135,978 B2 | 11/2006 | Gisselberg et al. |
| 7,214,191 B2 | 5/2007 | Stringer et al. |
| 7,775,215 B2 | 8/2010 | Hassler, Jr. et al. |
| 7,775,966 B2 | 8/2010 | Dlugos et al. |
| 7,850,006 B2 | 12/2010 | Uchiyama |
| 7,873,401 B2 | 1/2011 | Shachar |
| 7,887,516 B2 | 2/2011 | Young |
| 7,927,270 B2 | 4/2011 | Dlugos et al. |
| 8,016,744 B2 | 9/2011 | Dlugos et al. |
| 8,016,745 B2 | 9/2011 | Hassler, Jr. et al. |
| 8,174,346 B1 | 5/2012 | Koren |
| 8,240,211 B2 | 8/2012 | Zeitner et al. |
| 8,388,541 B2 | 3/2013 | Messerly et al. |
| 8,475,407 B2 | 7/2013 | Kalpin et al. |
| 8,483,802 B2 | 7/2013 | Kalpin et al. |
| 8,532,743 B2 | 9/2013 | Stangenes et al. |
| 8,622,975 B2 | 1/2014 | Andreoni et al. |
| 8,725,435 B2 | 5/2014 | Snow et al. |
| 8,781,555 B2 | 7/2014 | Burnside et al. |
| 8,840,541 B2 | 9/2014 | Snow et al. |
| 8,849,382 B2 | 9/2014 | Cox et al. |
| 8,939,888 B2 | 1/2015 | Augarten et al. |
| 9,017,283 B2 | 4/2015 | Birchard et al. |
| 9,113,812 B2 | 8/2015 | Kalpin et al. |
| 9,155,517 B2 | 10/2015 | Dunbar et al. |
| 9,216,257 B2 | 12/2015 | Kalpin et al. |
| 9,224,529 B2 | 12/2015 | Gery |
| 9,257,220 B2 | 2/2016 | Nicholls et al. |
| 9,299,925 B2 | 3/2016 | Yi et al. |
| 9,308,022 B2 | 4/2016 | Chitre et al. |
| 9,339,601 B2 | 5/2016 | Kalpin et al. |
| 9,439,653 B2 | 9/2016 | Avneri et al. |
| 9,456,766 B2 | 10/2016 | Cox et al. |
| 9,459,087 B2 | 10/2016 | Dunbar et al. |
| 9,492,097 B2 | 11/2016 | Wilkes et al. |
| 9,517,299 B2 | 12/2016 | Tieck et al. |
| 9,521,961 B2 | 12/2016 | Silverstein et al. |
| 9,554,716 B2 | 1/2017 | Burnside et al. |
| 9,597,008 B2 | 3/2017 | Henkel et al. |
| 9,636,031 B2 | 5/2017 | Cox |
| 9,649,048 B2 | 5/2017 | Cox et al. |
| 9,744,291 B2 | 8/2017 | Tieck et al. |
| 10,032,552 B2 | 7/2018 | Ma et al. |
| 10,449,330 B2 | 10/2019 | Newman et al. |
| 10,524,691 B2 | 1/2020 | Newman et al. |
| 10,751,509 B2 | 8/2020 | Misener |
| 11,344,220 B2 * | 5/2022 | Burkholz ................ A61M 5/32 |
| 11,369,410 B2 | 6/2022 | Lindekugel |
| 2003/0040671 A1 | 2/2003 | Somogyi et al. |
| 2003/0052785 A1 | 3/2003 | Gisselberg et al. |
| 2004/0019447 A1 | 1/2004 | Shachar |
| 2004/0051610 A1 | 3/2004 | Sajan |
| 2005/0059884 A1 | 3/2005 | Krag |
| 2006/0114088 A1 | 6/2006 | Shachar |
| 2006/0211914 A1 | 9/2006 | Hassler et al. |
| 2007/0244373 A1 | 10/2007 | Osypka |
| 2007/0290654 A1 | 12/2007 | Govari et al. |
| 2008/0146939 A1 | 6/2008 | McMorrow et al. |
| 2010/0043561 A1 | 2/2010 | Zeitner et al. |
| 2010/0210950 A1 | 8/2010 | Dunbar et al. |
| 2011/0060185 A1 | 3/2011 | Ikuma et al. |
| 2011/0196235 A1 | 8/2011 | Dunbar et al. |
| 2011/0237936 A1 | 9/2011 | Kalpin et al. |
| 2011/0237937 A1 | 9/2011 | Kalpin et al. |
| 2013/0150714 A1 | 6/2013 | Howlett et al. |
| 2013/0296691 A1 | 11/2013 | Ashe |
| 2014/0031674 A1 | 1/2014 | Newman et al. |
| 2014/0165796 A1 | 6/2014 | Gauthier et al. |
| 2014/0253270 A1 | 9/2014 | Nicholls et al. |
| 2014/0257080 A1 | 9/2014 | Dunbar et al. |
| 2014/0257104 A1 | 9/2014 | Dunbar et al. |
| 2014/0257746 A1 | 9/2014 | Dunbar et al. |
| 2015/0080710 A1 | 3/2015 | Henkel et al. |
| 2015/0359991 A1 | 12/2015 | Dunbar et al. |
| 2015/0365787 A1 | 12/2015 | Farrell |
| 2016/0351312 A1 | 12/2016 | Koren |
| 2017/0007200 A1 | 1/2017 | Hagy et al. |
| 2017/0079549 A1 | 3/2017 | Henkel et al. |
| 2017/0079550 A1 | 3/2017 | Henkel et al. |
| 2017/0079551 A1 | 3/2017 | Henkel et al. |
| 2017/0126864 A1 | 5/2017 | Lim et al. |
| 2017/0261564 A1 | 9/2017 | Gabrys et al. |
| 2017/0325713 A1 | 11/2017 | Burkholz et al. |
| 2017/0326342 A1 | 11/2017 | Ma et al. |
| 2018/0061546 A1 | 3/2018 | Ma et al. |
| 2018/0289929 A1 | 10/2018 | Ma et al. |
| 2018/0310955 A1 | 11/2018 | Lindekugel et al. |
| 2019/0298221 A1 | 10/2019 | Sonderegger |
| 2020/0360662 A1 | 11/2020 | Ma et al. |
| 2021/0065857 A1 | 3/2021 | Newman et al. |
| 2021/0169585 A1 | 6/2021 | Prince et al. |
| 2022/0105324 A1 | 4/2022 | Broniec et al. |
| 2022/0142502 A1 | 5/2022 | Prince et al. |
| 2022/0323101 A1 | 10/2022 | Lindekugel et al. |
| 2022/0401158 A1 | 12/2022 | Sowards et al. |
| 2023/0006443 A1 | 1/2023 | Patankar et al. |

FOREIGN PATENT DOCUMENTS

| | | |
|---|---|---|
| CN | 103945772 B | 9/2016 |
| CN | 105073067 B | 6/2017 |
| DE | 102006033229 B4 | 5/2013 |
| EP | 2015105 B1 | 6/2011 |
| EP | 2730306 A1 | 5/2014 |
| EP | 2285287 B1 | 4/2015 |
| EP | 2939599 A2 | 11/2015 |
| EP | 2939601 A2 | 11/2015 |
| EP | 2997901 A1 | 3/2016 |
| EP | 2753243 B1 | 4/2016 |
| JP | 5349582 B2 | 11/2013 |
| JP | 5908981 B2 | 4/2016 |
| JP | 6242421 B2 | 12/2017 |
| KR | 20150123233 A | 11/2015 |
| WO | 2008009442 A2 | 1/2008 |
| WO | 2009010386 A1 | 1/2009 |
| WO | 2009129845 A1 | 10/2009 |
| WO | 2013034175 A1 | 3/2013 |
| WO | 2013142386 A1 | 9/2013 |
| WO | 2014062728 A1 | 4/2014 |
| WO | 2014135592 A1 | 9/2014 |
| WO | 16096190 A1 | 6/2016 |
| WO | 17016961 A1 | 2/2017 |

(56) References Cited

FOREIGN PATENT DOCUMENTS

| WO | 2018/201053 | A1 | 11/2018 |
|----|-------------|----|---------|
| WO | 2022/099147 | A1 | 5/2022 |
| WO | 2022103772 | A1 | 5/2022 |
| WO | 2022271864 | A1 | 12/2022 |
| WO | 2023009446 | A1 | 2/2023 |

OTHER PUBLICATIONS

PCT/US2022/034584 filed Jun. 22, 2022, International Search Report and Written Opinion dated Oct. 10, 2022.
PCT/US2022/038202 filed Jul. 25, 2022 International Search Report and Written Opinion dated Nov. 14, 2022.
EP 18790656.5 filed Nov. 27, 2019 Supplementary European Search Report dated Apr. 9, 2020.
EP 221711096 filed May 2, 2022, Extended European Search Report dated Jul. 22, 2022.
EP20202521.9 filed Oct. 19, 2020 Extended European Search Report dated Jan. 28, 2021.
PCT/US2018/029958 filed Apr. 27, 2018 Communication Pursuant to Rules 70(2) and 70a(2) dated Apr. 29, 2020.
PCT/US2018/029958 filed Apr. 27, 2018 International Search Report and Written Opinion dated Jul. 11, 2018.
PCT/US2018/029958 filed Apr. 27, 2018 International Search Report dated Apr. 27, 2018.
U.S. Appl. No. 15/965,419, filed Apr. 27, 2018 Final Office Action dated Jan. 15, 2021.
U.S. Appl. No. 15/965,419, filed Apr. 27, 2018 Non-Final Office Action dated Aug. 6, 2021.
U.S. Appl. No. 15/965,419, filed Apr. 27, 2018 Non-Final Office Action dated Sep. 24, 2020.
U.S. Appl. No. 15/965,419, filed Apr. 27, 2018 Notice of Allowance dated Feb. 16, 2022.
PCT/US2021/058667 filed Nov. 9, 2021 International Search Report and Written Opinion dated Mar. 1, 2022.
U.S. Appl. No. 17/522,828, filed Nov. 9, 2021 Non-Final Office Action dated Nov. 9, 2023.
U.S. Appl. No. 17/850,468, filed Jun. 27, 2022 Restriction Requirement dated Dec. 29, 2023.

\* cited by examiner

MEDICAL DEVICE MAGNETIZER

PRIORITY

This application claims the benefit of priority to U.S. Provisional Application No. 63/111,498, filed Nov. 9, 2020, which is incorporated by reference in its entirety into this application.

BACKGROUND

Ultrasound imaging is a widely accepted tool for guiding interventional medical devices to target locations such as blood vessels or organs within the human body. Medical devices such as needles may be magnetized, inserted within the body such as by way of a percutaneous puncture, and monitored in real-time both immediately before and after the puncture so a clinician may determine the distance and the orientation of the needle to the target location and ensure successful access thereto.

A medical device may be magnetized by a movement near one or more magnets. For example, a clinician may magnetize a procedural needle by interfacing the needle with a needle magnetizer, by passing the needle between or next to magnet(s) using a dipping motion. The clinician may then subsequently track the needle with an ultrasound transducer.

However, during this movement, the medical device may make contact with potentially contaminating surfaces. For example, when a medical device is inserted into a magnetizer for magnetization, the medical device may contact an entrance of the magnetizer. Any exposure or contact by the medical device or the user to an unsterilized magnetization device may result in loss of sterility. Furthermore, a sterilized magnetizer may make contact with unsterilized surfaces (e.g., with an unsterile skin surface) and thereby become contaminated.

Existing magnetizer systems are often formed with thin, deep well enclosed in plastic and for which cleaning may be difficult. Existing magnetizer systems are therefore generally either single use, or may utilize a separate disposable piece to be inserted first into the magnetizer prior to dipping in a needle.

What is needed are devices, systems and methods thereof for sterilizing magnetization devices used with trackable medical devices.

SUMMARY

Briefly summarized, embodiments disclosed herein are directed to systems, methods and apparatuses for sterilizable magnetizers. In some embodiments, a magnetizer comprises at least at least one magnet; and a housing, the housing comprising: a top face; a bottom face positioned on an opposite side of the housing from the top face; a plurality of faces adjoining the top face and the bottom face; an interior comprising an interior surface formed at least in part by the top face, the bottom face and the plurality of faces; wherein the top face includes a first opening configured to receive a medical device; and wherein the at least one magnet is positioned within the interior of the housing.

In some embodiments, a face of the plurality of faces includes a second opening to expose at least a portion of the interior surface through the second opening. In some embodiments, the second opening is larger than the first opening. In some embodiments, the second opening is configured to obscure the at least one magnet. In some embodiments, the first opening and the second opening each have at least substantially different shapes. In some embodiments, the first opening is at least substantially circular and wherein the second opening is at least substantially ovaloid. In some embodiments, the at least one magnet is positioned on a face which is adjacent to the face which includes the second opening. In some embodiments, the at least one magnet is disposed within at least one face of the plurality of faces. In some embodiments, the at least one magnet is integrated into the at least one face of the plurality of faces. In some embodiments, the at least one magnet is positioned on the interior surface. In some embodiments, the at least one magnet is positioned on at least one face of the plurality of faces. In some embodiments, the at least one magnet further comprises a first magnet positioned on a first face of the plurality of faces and a second magnet positioned on a second face of the plurality of faces. In some embodiments, the first opening is formed at least in part by a curved conical tapering surface which extends from the top face toward the bottom face. In some embodiments, the first opening comprises a fillet. In some embodiments, the interior surface is at least substantially smooth.

In some embodiments, a system comprises a medical device; a detection system to detect the medical device; and a magnetizer, the magnetizer comprising: at least one magnet; and a housing, the housing comprising: a top face; a bottom face positioned on an opposite side of the housing from the top face; a plurality of faces adjoining the top face and the bottom face; an interior comprising an interior surface formed at least in part by the top face, the bottom face and the plurality of faces; wherein the top face includes a first opening configured to receive a medical device; and wherein the at least one magnet is positioned within the interior of the housing.

In some embodiments, a face of the plurality of faces of the magnetizer includes a second opening to expose at least a portion of the interior surface of the magnetizer through the second opening. In some embodiments, the second opening of the magnetizer is larger than the first opening of the magnetizer. In some embodiments, the second opening of the magnetizer is configured to obscure the at least one magnet. In some embodiments, the first opening and the second opening of the magnetizer each have at least substantially different shapes. In some embodiments, the first opening of the magnetizer is at least substantially circular and wherein the second opening of the magnetizer is at least substantially ovaloid. In some embodiments, the at least one magnet of the magnetizer is positioned on a face which is adjacent to the face which includes the second opening. In some embodiments, the at least one magnet of the magnetizer is disposed within at least one face of the plurality of faces. In some embodiments, the at least one magnet of the magnetizer is integrated into the at least one face of the plurality of faces. In some embodiments, the at least one magnet of the magnetizer is positioned on the interior surface of the magnetizer. In some embodiments, the at least one magnet of the magnetizer is positioned on at least one face of the plurality of faces. In some embodiments, the at least one magnet further comprises a first magnet positioned on a first face of the plurality of faces and a second magnet positioned on a second face of the plurality of faces. In some embodiments, the first opening of the magnetizer is formed at least in part by a curved conical tapering surface which extends from the top face toward the bottom face. In some embodiments, the first opening of the magnetizer comprises a fillet. In some embodiments, the interior surface of the magnetizer is at least substantially smooth.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," or a "proximal portion" of, for example, a medical device disclosed herein includes a portion of the medical device intended to be relatively nearer to a designated location. Likewise, a "proximal length" of, for example, the medical device includes a length of the medical device intended to be relatively nearer to or in the designated location. A "proximal end" of, for example, the medical device includes an end of the medical device intended to be relatively nearer to the designated location. The proximal portion, the proximal-end portion, or the proximal length of the medical device can include the proximal end of the medical device; however, the proximal portion, the proximal-end portion, or the proximal length of the catheter need not include the proximal end of the medical device. That is, unless context suggests otherwise, the proximal portion, the proximal-end portion, or the proximal length of the medical device is not a terminal portion or terminal length of the medical device.

With respect to "distal," or a "distal portion" of, for example, a medical device disclosed herein includes a portion of the medical device intended to be relatively further from a designated location. Likewise, a "distal length" of, for example, the medical device includes a length of the medical device intended to be relatively further from the designated location. A "distal end" of, for example, the medical device includes an end of the medical device intended to be relatively further from the designated location. The distal portion, the distal-end portion, or the distal length of the medical device can include the distal end of the medical device; however, the distal portion, the distal-end portion, or the distal length of the medical device need not include the distal end of the medical device. That is, unless context suggests otherwise, the distal portion, the distal-end portion, or the distal length of the catheter is not a terminal portion or terminal length of the medical device.

Unless defined otherwise, all technical and scientific terms used herein have the same meaning as commonly understood by those of ordinary skill in the art.

As set forth above, systems and methods thereof are needed to minimize contamination of sterilized medical devices during magnetization. Disclosed herein are systems and methods thereof.

Magnetizer

Figure 1:
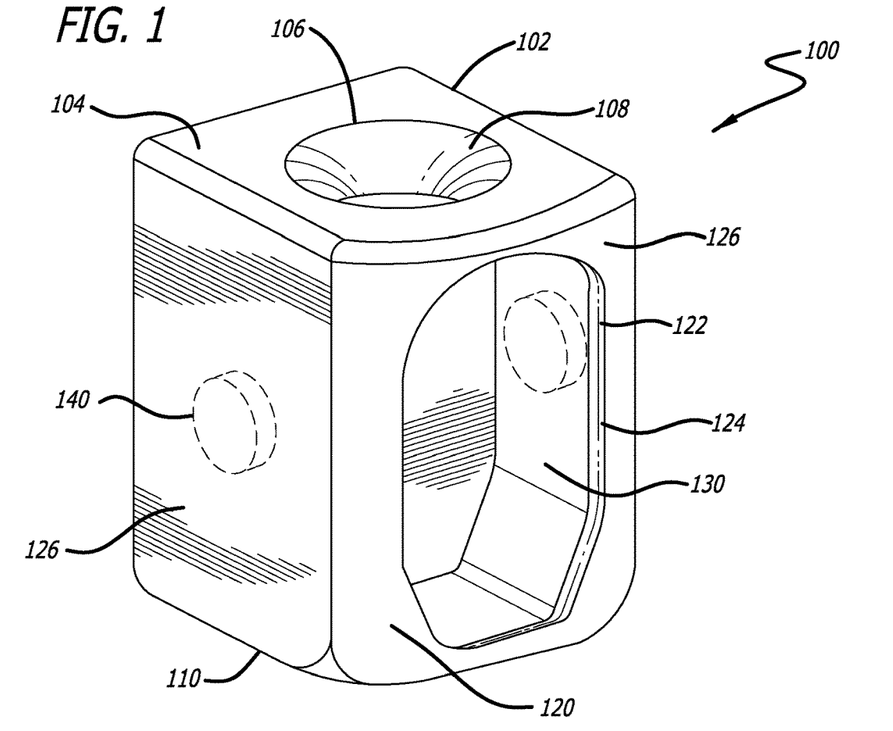
FIG. 1 illustrates a magnetizer housing, in accordance with some embodiments.

Referring to FIG. 1, a magnetizer housing is illustrated in accordance with some embodiments. In some embodiments, magnetizers may be implemented with magnetic-based device guidance systems for insertion and detection of medical devices (e.g., a magnetic-based needle guidance system for insertion and detection of sterilized needles). Examples of magnetic-based device guidance systems are disclosed in U.S. Pat. Nos. 8,388,541; 8,781,555; 8,849,382; 9,456,766; 9,492,097; 9,521,961; 9,554,716; 9,636,031; 9,649,048; 10,449,330; 10,524,691; and 10,751,509, each of which is incorporated by reference in its entirety into this application.

It is appreciated that a medical device of a magnetizable material enables the medical device (e.g., a needle) to be magnetized, which may then be tracked by an ultrasound-imaging system when the magnetized medical device is brought into proximity of magnetic sensors (e.g., a magnetic-sensor array) or inserted into the body of the patient during an ultrasound-based medical procedure. Such magnetic-based tracking of the magnetized medical device assists a clinician in placing a tip of the medical device in a desired location, such as in a lumen of a blood vessel, by superimposing a simulated needle image representing the real-time distance and orientation of the needle over an ultrasound image of the body of the patient being accessed by the magnetized medical device. Such a medical device can be, e.g., stainless steel; however, other suitable needle materials that are capable of being magnetized can be employed. So configured, the needle or the like can produce a magnetic field or create a magnetic disturbance in a magnetic field detectable as magnetic signals by the magnetic-sensor array of the ultrasound probe so as to enable the distance and orientation of the magnetized medical device to be tracked by the ultrasound-imaging system.

As shown, magnetizer 100 includes a housing 102 that comprises a top face 104 including a first opening 106 formed by the top face 104, the first opening 106 including a curved portion 108; a bottom face 110; an adjacent face 120 which is adjacent to both the top face 104 and the bottom face 110; a second opening 122 formed by adjacent face 120, the second opening 122 being further formed by a second opening edge 124 on adjacent face 120. In the embodiment of FIG. 1 the adjacent face 120 is one of a plurality of faces 126. In some embodiments, such as in FIG. 1, the plurality of faces 126 includes a total of four faces including the adjacent face 120. Each face of the plurality of faces, including the adjacent face 120, is adjacent to top face 104 and the bottom face 110. An interior surface 130 is formed by the top face 104, the bottom face 110, the adjacent face 120 and the plurality of faces 126. The magnetizer 100 further includes one or more magnetization elements 140 (e.g., magnets), which may be enclosed or encapsulated within the housing 102, as discussed further below.

In some embodiments, the first opening 106 is configured to allow a medical device to pass therethrough next to or between the magnetization elements 140. In some embodiments, the first opening 106 may be a hole, aperture, gap, slot or other opening formed by the top face 104 which permits a device to enter and move therethrough. In one example, the first opening 106 may include an at least substantially circular aperture shaped by the top face 104; however, the first opening 106 may take shapes other than a circle such as a rectangle, an oval, etc.

In some embodiments, the first opening 106 is configured to facilitate user insertion and removal of a medical device (e.g., a needle) into the magnetizer 100. For example, the first opening 106 may have a width suitable for enabling a user holding a needle to briefly insert and remove the needle in a dipping motion, thereby magnetizing the needle within the magnetizer. In an embodiment, the user may rest a medical device on opening 106 and curved portion 108 so the medical device moves through the opening 106 in a controlled manner. In some embodiments, the curved portion 108 may comprise a fillet and/or a rounded portion. In further embodiments, the first opening 106 may have proportions which are suitable for insertion of either a needle, or a needle having a needle cover. The magnetizer 100 may then be used even if the needle cover has not been removed from a needle. In some embodiments, the opening 106 and curved portion 108 may have a length extending toward the bottom face 110 at least as long as the medical device. Such a length may reduce the chance that a medical device will contact the faces forming the interior surface 130. In some embodiments, the top face 104, first opening 106 and/or interior surface 130 are least substantially free from structures which would impede the passage of a medical device (e.g., needle) therethrough.

In some embodiments, one or more of a tube, a shaft, or a bore may extend from top face 104 and opening 106 toward bottom face 110. In some embodiments a channel may be formed within the tube, shaft or bore, through which the medical device may pass.

In some embodiments, the first opening 106 may be positioned on the top face 104 to receive a medical device for magnetization. For example, first opening 106 may be positioned in the center of the top face 104; in a corner of top face 104; on an edge of top face 104; or in other positions so that a medical device may be received. In an embodiment first opening 106 does not overlap the second opening 122, so that an inserted medical device will touch the curved portion 108 without touching the adjacent face 120 or the second opening edge 124. In some embodiments, an inserted medical device may be held by a user and moved through the first opening 106 and the curved portion 108 toward the bottom face 110. In one embodiment, the user may magnetize the inserted medical device by inserting the medical device through the first opening 106 until the medical device contacts the bottom face 110, and then subsequently removes the medical device through first opening 106. However, the medical device need not contact the bottom face 110.

In some embodiments, the first opening 106 may include structures to aid passage of a medical device into the magnetizer 100 and near or past the magnetization elements 140. For example, in the embodiment of FIG. 1, first opening 106 includes the curved portion 108 (e.g., a fillet). In some embodiments, first opening 106 includes a curved, conical tapering surface, which extends from the top face 104 toward the bottom face 110. For example, the first opening 106 may be funnel-shaped, may taper or narrow, and/or may have a conical shape so that an inserted medical device is directed toward the center of opening 106. In an embodiment, a user may "dip" a medical device by placing the medical device on curved portion 108, causing the medical device to move toward the center of the opening 106, and then remove the medical device after it has been magnetized.

A first opening 106 having a tapered shape may direct the movement of the medical device to attempt to avoid between the medical device and other portions of the magnetizer 100 (e.g., interior surface 130). For example, in embodiments where a medical device to be magnetized is a needle, first opening 106 may have a width which is at least equal to a width of the needle, so that the needle may pass through. In some embodiments, the first opening is wider than the needle, to facilitate movement of the needle into and out of the magnetizer 100. In some embodiments, a portion of the first opening 106 may be narrower than the medical device so that a medical device may be less likely to unintentionally pass through.

In some embodiments, the first opening 106 and the curved portion 108 may be configured for cleaning. For example, in use or storage, the magnetizer 100 may accumulate contaminants on its surfaces. Curved portion 108 may provide a sloping surface for cleaning. For example, a cleaning device (e.g., sponges, brushes; sterilizations devices) may be placed through the first opening 106 and use the surface of curved portion 108 for support (as the cleaning device cleans the surfaces of first opening 106 and/or curved portion 108.

In some embodiments, the first opening 106 may be angled to accommodate a particular type of medical device. For example, first opening 106 and/or the curved portion 108 may be straight (e.g., at least substantially perpendicular to the base surface 112), or may be angled with an angle of, for example, 30°, 45°, 60°, 75°, 90°, etc. In embodiments first opening 106 and/or curved portion 108 may be include multiple angles, such as to accommodate a curved device.

In some embodiments, the bottom face 110 may be configured to maintain magnetizer sterility. In the embodiment of FIG. 1, bottom face 110 may be raised off of the ground to minimize potential points of contamination, such that those portions which are directly touching the ground are more likely to be contaminated.

In some embodiments, any number of faces may form the plurality of faces 126. For example, the embodiment of FIG. 1 includes four faces forming plurality of faces 126. However, in some embodiments, three, five or more faces may be used. In some embodiments, the faces of plurality of faces 126 may be flat, rounded, curved or have other shapes. Furthermore, the top face 104 and the bottom face 110 may also be shaped to be flat, rounded, curved or in other shapes. In an embodiment the top face 104 may be flat and smooth (e.g., without sharp corners or recesses) so that an inserted object will contact the first opening 106 without contacting potentially contaminating surfaces. First opening 106 may be configured to accommodate the plurality of faces.

In the embodiment of FIG. 1, the adjacent face 120 include a second opening 122. Second opening 122 provides, among other things, an entrance for objects (e.g., cleaning devices) to access the interior surface 130. Impurities and contaminants can thereby be removed, and interior surface 130 sterilized. In some embodiments, the interior surface 130 may comprise a well, and second opening 122 may provide a location for a user to access the well.

In some embodiments, the second opening 122 may have a shape to permit access of different kinds of cleaning devices. In some other embodiments second opening 122 may be square; rectangular; elliptical; circular; etc. In an embodiment as shown in FIG. 1, the second opening 122 may have an ovaloid shape. In some embodiments, second opening 122 may be configured to expose all of the interior surface 130, or to only expose certain portions of the interior surface 130.

In some embodiments, the second opening 122 may have a size to permit access of different kinds of cleaning devices. In some other embodiments, second opening 122 may be larger than the first opening 106. For example, second opening 122 may comprises at least a third of the size of adjacent face 120, at least half of the size of the adjacent face 120; or at least three-quarters of the size of adjacent face 120. In some embodiments, first opening 106 may be configured to receive predetermined kinds of medical devices (e.g., needles) which are smaller than cleaning devices used for cleaning the interior surface 130. In some embodiments, second opening 122 may be larger than first opening 106.

In some embodiments, the second opening 122 may have a size and shape for allowing a user to view the interior surface 130 of the magnetizer 100. Among other things, a user may view the interior surface 130 and any parts of magnetizer 100 (e.g., the bottom face 110; the magnetization elements 140) during magnetization of a medical device and/or cleaning. Furthermore, in some embodiments, second opening 122 may have a size and shape which hides one or more parts of the magnetizer 100 from view or exposure. For example, the second opening 122 may have a second opening edge 124 to obscure or hide the magnetization elements 140 from view. Hiding parts of magnetizer 100 and interior surface 130 behind the second opening edge 124 may reduce their exposure to contaminants.

In some embodiment's multiple faces of the plurality of the faces 126 may include an opening similar to the second opening 122. For example, two or more of the faces of the plurality of faces 126 may include an opening to receive a cleaning device, enable a user to sterilize the interior surface 130, or add, replace or remove objects within the magnetizer 100.

In embodiments the second opening 122 may comprise a movable fixture to enable or prevent access to the interior surface 130. For example, the second opening 122 may include a door which may be opened to expose interior surface 130, and closed to hide interior surface 130 from view. Furthermore, second opening 122 may comprise a flap, cover or other barrier which prevents or minimizes contaminants from entering interior surface 130 via second opening 122.

Figure 2:
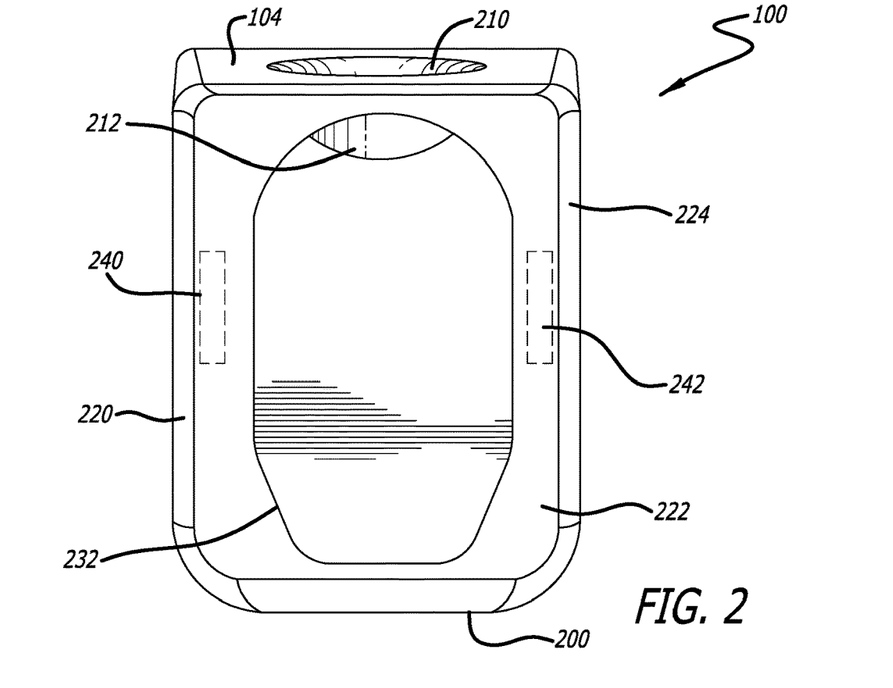
FIG. 2 illustrates a front view of a magnetizer, in accordance with some embodiments.

Referring to FIG. 2, a front view of a magnetizer is illustrated in accordance with some embodiments. Magnetizer 100 includes a top face 104, base 200, curved top opening 210, side faces 220, 222 and 224, side opening 230, side edge 232 and magnets 240 and 242 behind side edge 232. Curved top opening 210 includes a slope 212. Side opening 230 is positioned on side face 222.

In some embodiments, the curved top opening 210 protrudes below the top face 104. For example, as shown in FIG. 2, curved top opening 210 may protrude beneath top face 104 toward the base 200 and be visible through the side opening 230. In some embodiments, a protruding curved top opening 210 may be cleaned or sterilized through the side opening 230 as well as from in the direction of top face 104. For example, in order to clean curved top opening 210 a cleaning device may be provided through curved top opening 210 and/or through side opening 230. The visibility of curved top opening 210 through side opening 230 may provide alternative angles which increase the amount of surface area that can be cleaned. In some embodiments, side opening 230 may provide exposure for all of the interior of the magnetizer 100. In some embodiments curved top opening 210 may comprise a fillet.

In the embodiment of FIG. 2, the magnets 240 and 242 are positioned on the side faces 220 and 224. In some embodiments, magnets 240 and 242 may be positioned according to the medical device to be magnetized. For example, magnets 240 and 242 may be positioned closer to the top face 104 to magnetize medical devices having shorter lengths or that have designs which a user may have difficulty moving through magnetizer 100. Moreover magnets 240 and 242 may be positioned closer to base 200 for embodiments in which medical devices having longer lengths are magnetized, in which the medical device may move deeper through magnetizer 100. Furthermore magnets 240 and 242 may be positioned on different locations of side faces 220 and 224, e.g., magnets 240 and 242 may be positioned in a center; in a corner; or on an edge of corresponding side faces 220 and 224. In some embodiments, magnets 240 and 242 may have different relative positions (e.g., in an embodiment magnet 240 may be positioned in a center of side face 220 whereas magnet 242 is positioned in a corner of side face 224). In some embodiments magnets 240 and 242 may be formed as part of side faces 220 and 224 (e.g., magnets 240 and 242 may be integrated into the side face 220 and 224.

In the embodiment of FIG. 2 the side opening 230 is formed by a side edge 232 of the side face 222. In some embodiments, the magnets 240 and 242 may be partially or fully hidden from view by side edge 232. Among other things, potential contaminants may thereby be hindered from contacting magnets 240 and 242 by side edge 232. Furthermore, a user may hold the magnetizer 100 using side edge 232, such as for transportation, rather than touching portions of magnetizer 100 nearer the magnets 240 and 242. Magnets 240 and 242 may be positioned for later cleaning. For example, magnets 240 and 242 may be placed on opposite faces (e.g., in the embodiment of FIG. 2, on faces 220 and 224) with sufficient distance to allow for cleaning.

In some an embodiment, the side edge 232 does not extend to base 200. In use, for example, the base 200 may be rested on a surface for magnetization of medical devices. Contaminants on the surface which base 200 rests on will be prevented from entering the magnetizer 100 by base 200 and side edge 232.

Figure 3:
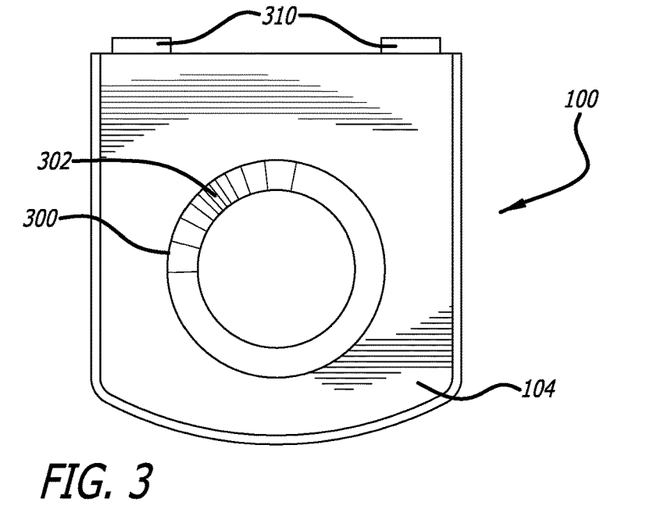
FIG. 3 illustrates a top view of a magnetizer, in accordance with some embodiments.

Referring to FIG. 3, a top view of a magnetizer is shown in accordance with some embodiments. The magnetizer 100 includes a top face 104 having a ring-shaped opening 300 with a slope 302. In an embodiment of FIG. 3, the ring-shaped opening 300 is configured for a user to vertically dip a needle through the ring-shaped opening 300 for magnetization, and then enable a user to pull the needle out for removal. In the embodiment of FIG. 3, the magnetizer 100 include a brace 310. Brace 310 provides support for magnetizer 100, e.g., by pressing against a surface near magnetizer 100. For example, in some embodiments, the magnetizer 100 may be attached to a clip, where the brace 310 may slide over or through a clip that is mounted to an ultrasound console. In such embodiments, a portion of the brace 310 may abut the ultrasound console.

Figure 4:
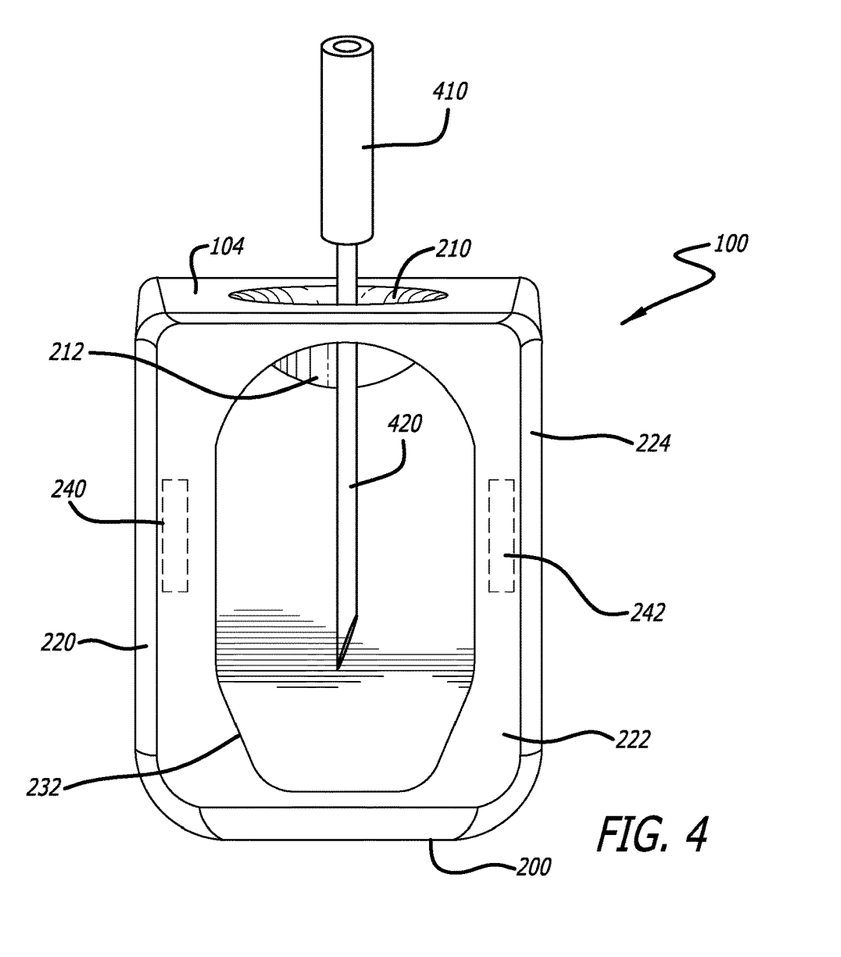
FIG. 4 illustrates a magnetizer housing and medical device, in accordance with some embodiments.

Referring to FIG. 4, a magnetizer housing and medical device are shown, in accordance with some embodiments. A system 400 includes a magnetizer 100 and a needle 410. The magnetizer 100 includes a top face 104, a curved top opening 210 having a slope 212, side faces 220, 222 and 224, side opening 230, side edge 232 and magnets 240 and 242 behind side edge 232. The needle 410 include a magnetizable portion 420.

In some embodiments, the needle 410 is inserted through the curved top opening 210 and thereby passes through the top face 104. The slope 212 may provide support for needle 410 as it moves therethrough. The magnets 240 and 242, located on side faces 220 and 224, magnetize the magnetizable portion 420 as the needle 410 moves into the magnetizer 100. The needle 410 may be removed after the magnetizable portion 420 is magnetized. A user may view the needle 410 through the side opening 230 during insertion and removal, and may further access the interior (e.g., with reference to FIG. 1, the interior surface 130) of magnetizer 100 at any time to clean any components of the magnetizer.

Ultrasound-Imaging Systems

In some embodiments, a magnetic-based device guidance system may be an ultrasound imaging system. In some embodiments, the ultrasound-imaging system may include a console, a display screen, an ultrasound probe, and magnetizer. In some embodiments, an ultrasound imaging system may further include a magnetizer cover. An ultrasound-imaging system may be used to image a target such as a blood vessel or an organ within a body of a patient prior to a percutaneous puncture with a medical device (e.g., needle) for inserting the needle into the target and accessing the target. Ultrasound-imaging systems may be used with a variety of ultrasound-based medical procedures, such as catheterization or to perform a biopsy of patient tissue. During use of the ultrasound imaging system, the clinician may need to reach out of a sterile field around the patient to control the ultrasound-imaging system. In some embodiments, the display screen may be used to display the distance and orientation of a magnetized medical device such as a needle. Distance and orientation data may be superimposed in real-time atop an ultrasound image of the target, thus enabling a clinician to accurately guide the magnetized medical device to the intended target In some embodiments, the ultrasound probe is coupled to the console. The probe may be placed against a skin surface to generate ultrasound signals into a patient, receive reflected ultrasound signals or ultrasound echoes from the patient by way of reflection of the generated ultrasonic pulses by the body of the patient, and convert the reflected ultrasound signals into corresponding electrical signals for processing into ultrasound images by the console to which the ultrasound probe is communicatively coupled. In this way, a clinician can employ the ultrasound-imaging system to determine a suitable insertion site and establish vascular access with the needle or another medical device.

In some embodiments, an ultrasound probe can include a magnetic-sensor array for detecting a magnetized medical device such as a needle during ultrasound-based medical procedures. The magnetic-sensor array includes a number of magnetic sensors embedded within or included on a housing of the ultrasound probe. The magnetic sensors are configured to detect a magnetic field or a disturbance in a magnetic field as magnetic signals associated with the magnetized medical device when it is in proximity to the magnetic-sensor array. The magnetic sensors are also configured to convert the magnetic signals from the magnetized medical device (e.g., the needle) into electrical signals for the console to process into distance and orientation information for the magnetized medical device with respect to the pre-defined target, as well as for display of an iconographic representation of the magnetized medical device on the display screen. Thus, the magnetic-sensor array enables the ultrasound-imaging system to track the needle or the like. The magnetic sensors may include three orthogonal sensor coils for enabling detection of a magnetic field in three spatial dimensions. In some embodiments, instead of 3-D sensors, a plurality of 1-dimensional ("1-D") magnetic sensors can be included and arranged as desired to achieve 1-, 2-, or 3-D detection capability.

During operation of the ultrasound-imaging system, the ultrasound probe is placed against skin of the patient. An ultrasound beam is produced so as to ultrasonically image a portion of a target such as a blood vessel beneath a surface of the skin of the patient. The ultrasonic image of the blood vessel can be depicted and stabilized on the display screen of the ultrasound-imaging system.

The ultrasound-imaging system may be configured to detect the distance and orientation of a medical device, such as by way of the magnetic sensors. By way of example, the magnetic-sensor array of the ultrasound probe is configured to detect a magnetic field of the magnetized medical device or a disturbance in a magnetic field due to the magnetized magnetic device. Each magnetic sensor of the magnetic sensors in the magnetic-sensor array 146 is configured to spatially detect the needle in 3-dimensional space. Thus, during operation of the ultrasound-imaging system, magnetic field strength data of the medical device's magnetic field sensed by each magnetic sensor of the magnetic sensors is forwarded to a processor of the console, which computes in real-time the distance and orientation of the magnetized medical device. The distance and orientation of the magnetized medical device is also for graphical display on the display screen.

The distance or orientation of any point along an entire length of the magnetized medical device in a coordinate space with respect to the magnetic-sensor array can be determined by the ultrasound-imaging system using the magnetic-field strength data sensed by the magnetic sensors. Moreover, a pitch and yaw of the needle can also be determined. Suitable circuitry of the ultrasound probe, the console, or other components of the ultrasound-imaging system can provide the calculations necessary for such distance or orientation.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A magnetizer, comprising:
   at least one magnet; and
   a housing, the housing comprising:
     a top face;
     a bottom face positioned on an opposite side of the housing from the top face;
     a plurality of faces adjoining the top face and the bottom face; and
     an interior comprising an interior surface formed at least in part by the top face, the bottom face, and the plurality of faces, wherein:
       the top face includes a first opening configured to receive a medical device,
       the at least one magnet is positioned within the interior of the housing, and
       a face of the plurality of faces includes a second opening to expose at least a portion of the interior surface through the second opening, the second opening comprising at least ⅓ of a size of the face.

2. The magnetizer of claim 1, wherein the second opening is larger than the first opening.

3. The magnetizer of claim 1, wherein the second opening is configured to obscure the at least one magnet.

4. The magnetizer of claim 1, wherein the first opening and the second opening each have at least substantially different shapes.

5. The magnetizer of claim 4, wherein the first opening is at least substantially circular and wherein the second opening is at least substantially ovaloid.

6. The magnetizer of claim 1, wherein the at least one magnet is positioned on a face which is adjacent to the face of the plurality of faces that includes the second opening.

7. The magnetizer of claim 1, wherein the at least one magnet is disposed within at least one face of the plurality of faces.

8. The magnetizer of claim 7, wherein the at least one magnet is integrated into the at least one face of the plurality of faces.

9. The magnetizer of claim 1, wherein the at least one magnet is positioned on the interior surface.

10. The magnetizer of claim 9, wherein the at least one magnet is positioned on at least one face of the plurality of faces.

11. The magnetizer of claim 10, wherein the at least one magnet further comprises a first magnet positioned on a first face of the plurality of faces and a second magnet positioned on a second face of the plurality of faces.

12. The magnetizer of claim 1, wherein the first opening is formed at least in part by a curved conical tapering surface which extends from the top face toward the bottom face.

13. The magnetizer of claim 1, wherein the first opening comprises a fillet.

14. The magnetizer of claim 1, wherein the interior surface is at least substantially smooth.

15. A system, comprising:
    a medical device;
    a detection system to detect the medical device; and
    a magnetizer, the magnetizer comprising:
      at least one magnet; and
      a housing, the housing comprising:
        a top face;
        a bottom face positioned on an opposite side of the housing from the top face;
        a plurality of faces adjoining the top face and the bottom face; and
        an interior comprising an interior surface formed at least in part by the top face, the bottom face and the plurality of faces, wherein:
          the top face includes a first opening configured to receive the medical device,
          the at least one magnet is positioned within the interior of the housing, and
          a face of the plurality of faces includes a second opening to expose at least a portion of the interior surface through the second opening, the second opening comprising at least ⅓ of a size of the face.

16. The system of claim 15, wherein the second opening of the magnetizer is larger than the first opening of the magnetizer.

17. The system of claim 15, wherein the second opening of the magnetizer is configured to obscure the at least one magnet.

18. The system of claim 15, wherein the first opening and the second opening of the magnetizer each have at least substantially different shapes.

19. The system of claim 18, wherein the first opening of the magnetizer is at least substantially circular and wherein the second opening of the magnetizer is at least substantially ovaloid.

20. The system of claim 15, wherein the at least one magnet of the magnetizer is positioned on a face which is adjacent to the face of the plurality of faces that includes the second opening.

21. The system of claim 15, wherein the at least one magnet of the magnetizer is disposed within at least one face of the plurality of faces.

22. The system of claim 21, wherein the at least one magnet of the magnetizer is integrated into the at least one face of the plurality of faces.

23. The system of claim 15, wherein the at least one magnet of the magnetizer is positioned on the interior surface of the magnetizer.

24. The system of claim 23, wherein the at least one magnet of the magnetizer is positioned on at least one face of the plurality of faces.

25. The system of claim 24, wherein the at least one magnet further comprises a first magnet positioned on a first face of the plurality of faces and a second magnet positioned on a second face of the plurality of faces.

26. The system of claim 15, wherein the first opening of the magnetizer is formed at least in part by a curved conical tapering surface which extends from the top face toward the bottom face.

27. The system of claim 15, wherein the first opening of the magnetizer comprises a fillet.

28. The system of claim 15, wherein the interior surface of the magnetizer is at least substantially smooth.

* * * * *